US006589203B1

(12) United States Patent
Mitrev

(10) Patent No.: US 6,589,203 B1
(45) Date of Patent: Jul. 8, 2003

(54) GLAUCOMA DRAINAGE DEVICE IMPLANT

(76) Inventor: Peter Mitrev, 1218 Pacels Way, Chesapeake, VA (US) 23322

( * ) Notice: Subject to any disclaimer, the term of this patent is extended or adjusted under 35 U.S.C. 154(b) by 91 days.

(21) Appl. No.: 09/630,381

(22) Filed: Aug. 1, 2000

Related U.S. Application Data
(60) Provisional application No. 60/178,141, filed on Jan. 26, 2000.

(51) Int. Cl.[7] ................................................ A61M 1/00
(52) U.S. Cl. .................................. 604/27; 604/8; 604/9
(58) Field of Search .......................... 604/8, 9, 10, 246, 604/247, 294, 296, 298, 288.03

(56) References Cited

U.S. PATENT DOCUMENTS

| 4,457,757 | A |   | 7/1984  | Molteno           |        |
|-----------|---|---|---------|-------------------|--------|
| 4,750,901 | A |   | 6/1988  | Molteno           |        |
| 5,178,604 | A |   | 1/1993  | Baerveldt         |        |
| 5,397,300 | A |   | 3/1995  | Baerveldt         |        |
| 5,454,796 | A |   | 10/1995 | Krupin            |        |
| 5,476,445 | A |   | 12/1995 | Baerveldt et al.  |        |
| 5,558,629 | A |   | 9/1996  | Baerveldt et al.  |        |
| 5,616,118 | A |   | 4/1997  | Ahmed             |        |
| 5,626,559 | A |   | 5/1997  | Solomon           |        |
| 5,681,275 | A |   | 10/1997 | Ahmed             |        |
| 5,752,928 | A | * | 5/1998  | de Roulhac et al. | 604/8  |
| 5,830,173 | A | * | 11/1998 | Avery et al.      | 604/294 |
| 6,050,970 | A | * | 4/2000  | Baerveldt         | 604/10 |
| 6,142,969 | A | * | 11/2000 | Nigam             | 604/8  |

FOREIGN PATENT DOCUMENTS

WO           WO 92/19294         * 11/1992  ................ 604/8

* cited by examiner

Primary Examiner—Thomas Denion
Assistant Examiner—Jaime Corrigan
(74) Attorney, Agent, or Firm—Lambert & Associates; Gary Lambert, Esq; Edward Timmer, Esq

(57) ABSTRACT

A glaucoma drainage device implant foldable and rollable upon itself for the drainage of aqueous humor in the treatment of glaucoma comprising an episcleral plate having both an upper surface and a lower surface and a drainage tube having one end terminating above the upper surface of the episcleral plate whereby the glaucoma drainage device may be delivered to the implant site through the lumen of a needle or cannula. The glaucoma drainage device implant may further comprise retainers for maintaining the implant in the proper operable position; a terminal collar for retention purposes; and a peripheral rim, inflatable in some embodiments, for improved filtration.

19 Claims, 3 Drawing Sheets

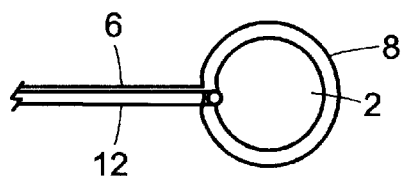
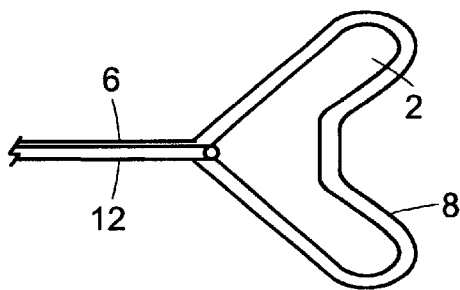
FIG. 5　　　　　　　　　　FIG. 6
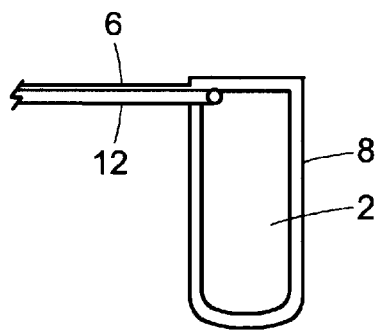
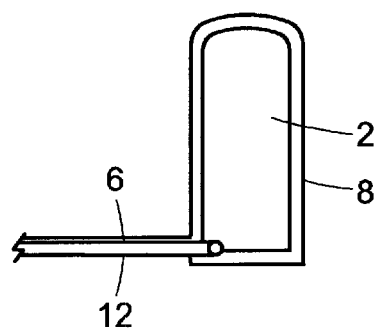
FIG. 7　　　　　　　　　　FIG. 8
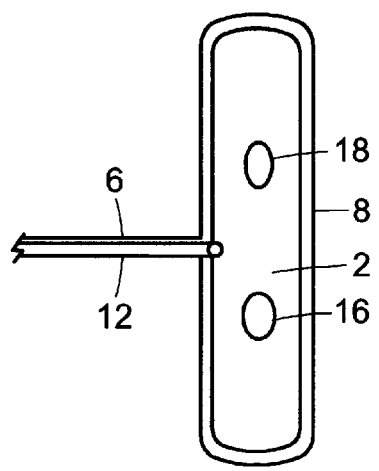
FIG. 9

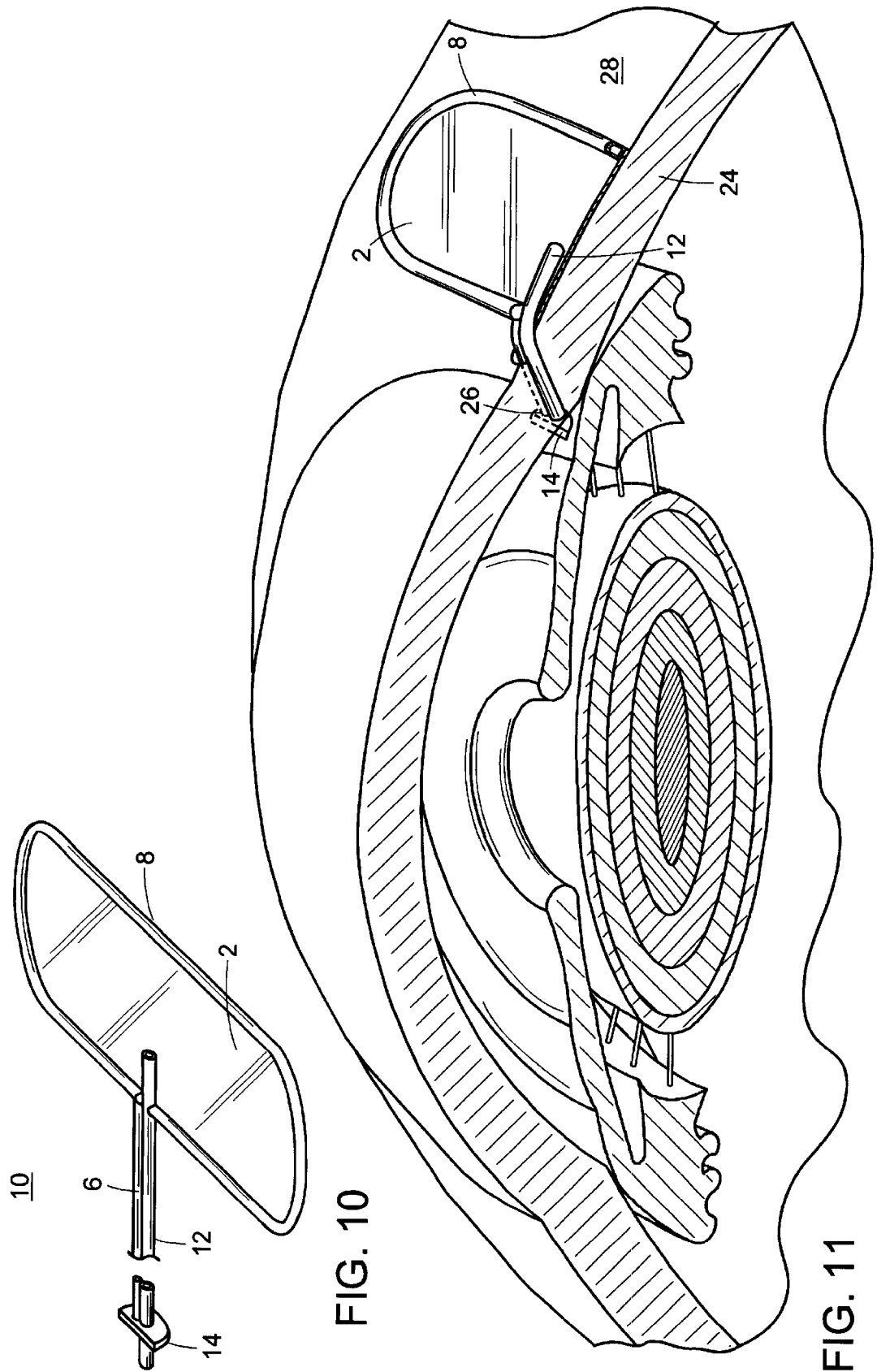

GLAUCOMA DRAINAGE DEVICE IMPLANT

CROSS REFERENCE TO RELATED APPLICATIONS

This application claims the benefit under 35 U.S.C. § 119 (e) of currently pending Provisional Application Ser. No.: 60/178,141 filed Jan. 26, 2000 by the same inventor.

BACKGROUND OF THE INVENTION

The glaucoma drainage device of the present invention pertains to devices useful in the treatment of recipients having glaucoma. More particularly, the present invention pertains to a glaucoma drainage device that is implanted in the eye of a recipient that minimizes the size of the incision required to implant the device.

Glaucoma is a condition in which the optic nerve is damaged. The optic nerve is damaged due to excessively high intraocular pressure in the eye. Excessive pressure occurs when the aqueous humor, the clear liquid in the eye, does not properly drain from the eye. Regardless of the reasons why the intraocular pressure builds in the eye, if left untreated the excessive intraocular pressure will likely damage the optic nerve and cause irreversible loss of eyesight.

A method of treating glaucoma when other less invasive methods of treatment such as drugs do not relieve the excessive intraocular pressures in glaucoma patients is incisional filtration implant surgery. In this type of surgery a tube is inserted through an incision, a sclerostomy, in the sclera of the recipient's eye. The purpose of implanting the drainage tube is to provide a means for the aqueous humor to drain from the eye and thus alleviate the excessive intraocular pressures. The filtration surgery may involve implanting a drainage tube connected to a plate that acts a reservoir that is drained via the drainage tube. A problem associated with implanting conventional glaucoma drainage devices comprising a plate and a tube is the incision required to deliver the device to the implant site. The more extensive the surgery incision required to implant the device the greater the risks of postoperative infection, inflammation and length of healing time of the surgery implant site.

SUMMARY OF THE INVENTION

The glaucoma drainage device of the present invention comprises a episcleral plate, foldable and rollable upon itself, and a drainage tube connected to the foldable and rollable plate at one end and free at the other end that may be implanted in a recipient's eye through an injection delivery system for drainage of aqueous humor for the treatment of glaucoma. The present invention may further comprise a peripheral ridge along the upper surface of the episcleral plate to add volume to the plate for improved drainage; retention rings and bands for maintaining the glaucoma drainage device at its intended and implanted location; and a terminal collar located at or near the free end of the drainage tube for preventing migration of the device into the cornea of the recipient.

The present invention will provide an effective treatment for glaucoma by improving postoperative filtration and successful reduction of intraocular pressure. Additionally, the common risks associated with glaucoma incisional surgery to reduce the intraocular pressure in glaucoma patients such as postoperative infection, inflammation and the length of surgery site healing time are all believed to be reduced due to the single injection stab incision associated with the present invention as compared to traditional glaucoma incisional surgery using traditional glaucoma drainage devices requiring more extensive incisions. The device of the present invention is capable of being rolled and folded upon itself so that the entirety of the device may be delivered to the implant site via an injection delivery system such as a needle. The episcleral plate itself is sized and shaped to fit on a recipient's eye to provide adequate filtering and drainage and yet the entire invention is capable of being delivered to the implant site via an injection delivery system.

The episcleral plate may be constructed of silicone or other bio-compatible materials that have proven to be well suited for glaucoma drainage devices. Furthermore, in order to effectuate the rolling and folding capabilities of the present invention so that the required incision in the sclera, a sclerostomy, is optimally minimized to an needle injection-sized incision the episcleral plate may be constructed of a material having a memory of its unfolded shape. The memory of the plate material will work to resist permanent deformity of the plate as a result of folding and rolling the plate upon itself for implantation and also work to ensure the plate returns to its intended shape for a proper fit in the recipient's eye. Special folding techniques may also be used to ensure minimizing deformation of the device. Still other embodiments may have resilient or inflatable veins appropriately disposed in the device so that the device can open to its desired shape once implanted in the recipient's eye.

Other beneficial and useful aspects of the present invention include having an inflatable rim. An embodiment of the present invention having an inflatable rim may be folded and rolled upon itself with the rim in a non-inflated or deflated state for ease of delivery to the implant site. After insertion into a recipient's eye at the desired location, the inflatable rim of the present invention may be inflated to provide a ridged wall to add volume to the glaucoma drainage device for better filtration. The rim may be inflated with air, B.S.S. or other fluids.

The drainage tube of the present device may be a tube with a passageway therethrough for drainage of aqueous humor from the episcleral plate located and implanted on top of the sclera through an sclerostomy to the anterior chamber. The tube may also incorporate pressure regulation capabilities such as valves whereby aqueous humor is allowed to drain through the drainage tube when the intraocular pressure exceeds a predetermined threshold pressure. The drainage tube may further comprise a passageway for drainage of aqueous humor and a passageway for inflating the inflatable rim of embodiments having an inflatable rim. The combined aqueous humor drainage tube and inflation tube may, individually or in combination, be enveloped in a drainage tube sleeve like other embodiments solely having an aqueous drainage tube.

In order to avoid the post operative complication of hypotony due to over filtration, the free end of the aqueous shunting tube implanted in the anterior chamber may be covered with a water impermeable, pigmented membrane. This membrane can either be manually opened with a sharp instrument or melted open with an ophthalmic laser to allow the free egress of aqueous humor from the anterior chamber when deemed appropriate by the surgeon.

The drainage tube of the device may also have bands, rings or other retention structures affixed thereto for retaining the drainage tube and the implanted device in the desired location. The retention bands, rings or other structures may be sized and configured to prevent and aid in preventing leakage around the drainage tube. The device may also include a terminal collar. The terminal collar is typically located at or near the end of the drainage tube not connected to the episcleral plate.

Another benefit of the present invention is that the device may also be implanted by rolling and folding the device and then feeding the rolled and folded device along a guide wire into the sub-tenon's space of the recipient's eye. As with the implantation technique involving passing the rolled and folded device through the lumen of a cannula or needle, the device is delivered to the implant site on the recipient's sclera while the free end of the tube is in place by the terminal collar and/or retention bands to prevent the tube from migrating into the cornea of the recipient.

In addition to the above descriptions and benefits, it is important to realize that the present invention may be implanted using conventional and traditional techniques. The advantage gained is that the conjunctival incision made to accommodate the device can be made much smaller.

BRIEF DESCRIPTION OF THE DRAWINGS

FIG. 2 is an elevational view thereof depicting the inflatable rim,

FIG. 5 is an embodiment of the present invention adapted for pediatric applications;

FIG. 6 is an embodiment of the present invention adapted for superior insertion;

FIG. 7 is an embodiment of the present invention having a left-sided plate;

FIG. 8 is an embodiment of the present invention having a right-sided plate;

FIG. 9 is an embodiment of the present invention having a fenestrated plate;

FIG. 10 is a perspective of the preferred embodiment of the present invention; and FIG. 11 is a cross-sectional depiction of the present invention in-situ.

DETAILED DESCRIPTION OF THE PREFERRED EMBODIMENT

Figure 1:
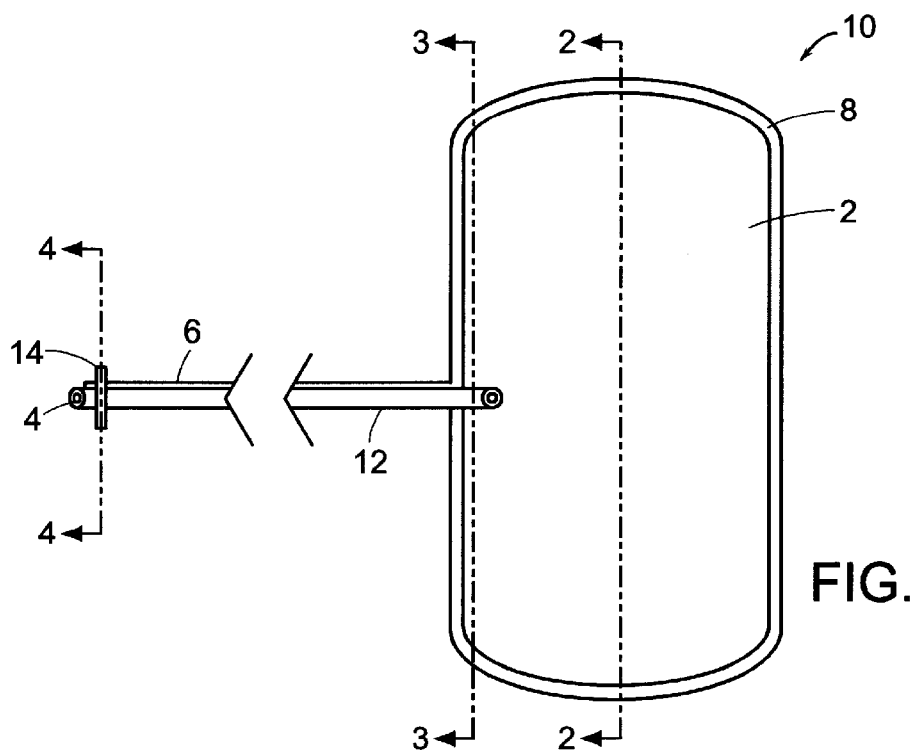
FIG. 1 is a top plan view of a preferred embodiment of the present invention.

The present invention is optimally implanted into the eye of a glaucoma patient by first rolling and folding the episcleral plate upon itself. The rolled and folded glaucoma drainage device of the present invention is then injected into the recipient's eye at the desired location through an injection delivery system, e.g. a lumen of a cannula or needle. The scleral incision commonly associated with glaucoma incisional implant surgery is thus virtually eliminated. Instead of an incision, the present invention only requires a needle injection-sized penetration for the delivery and implantation of the device. The preferred embodiment can more fully be understood by referring to the included figures and drawings. FIG. 1 shows a plan view of the device 10. The episcleral plate 2 and the rim 8 located at the peripheral edge of the plate 2 are clearly shown in FIG. 1. A typical drainage tube 12 is also shown. The length of the drainage tube 12 may vary depending on the physical constraints of the recipient. The drainage tube 12 is shown having one end attached to the episcleral plate 2 and a free end. Looking at the free end, there is shown an opening to drainage passageway 4. This drainage passageway extends all the way through the drainage tube 12.

Figure 4A:
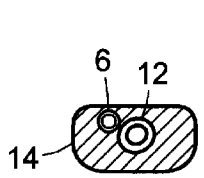
FIG. 4 is a depiction of various drainage tube configurations.
Figure 4B:
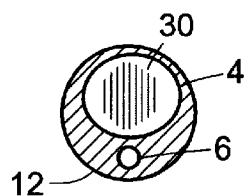
Figure 4C:
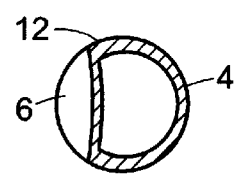

FIG. 4B depicts one embodiment of the drainage tube 12 having a manually penetratable impermeable membrane 30 occluding the free end of the drainage tube 12.

Figure 2A:
FIG. 2A shows the rim deflated and FIG. 2B shows the rim inflated.
Figure 2B:
Figure 3:
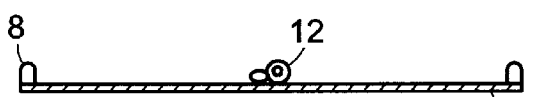
FIG. 3 is an elevational view of an embodiment of the present invention.

The rim 8 of the preferred embodiment is inflatable. It may be inflated with a liquid or a gas, including air. The FIG. 2A depicts the rim inflated while 2B shows it deflated. The drainage tube 12 may have a single drainage passageway 4 or also, in combination or alone, have a passageway 6 leading to the inflatable rim 8 for inflation of the rim 8.

The drainage tube 12 of the preferred embodiment also has a terminal collar 14 located near the free end of the drainage tube 12. The terminal collar 14 is affixed to the drainage tube 12 for retaining and maintaining the drainage tube in the proper and desired implantation location. It is vitally important to the post-operative success and effectiveness of the glaucoma incisional implant surgery that the glaucoma drainage device is maintained in the intended implanted position in the recipient's eye.

The FIGS. 5 through 9 each depicts other embodiments of the device of the present invention. FIG. 5 is an embodiment of the present invention adapted for pediatric applications. In order to accommodate the reduced anatomy of the pediatric eye, the implant may be downsized. The implant is downsized in all regards with the exception of the drainage tube 12. The surface area, as well as the shape of the episcleral plate 2 may accordingly be changed in order to safely implant the device between the extraocular muscles in order to minimize the affect on eye mobility and possible strabismus.

FIG. 6 is an embodiment of the present invention adapted for superior insertion. This embodiment of the present invention having an episcleral plate 2 area and shape as shown may be advantageous when restrictions caused by preexisting scar tissue or anatomy necessitates the implantation of the device directly in-line with the insertion of anyone of the extraocular recti muscles. This embodiment will allow the episcleral plate 2 to "straddle" the muscles without impinging on the muscles activity while still maintaining adequate surface area for filtration. The indentation shape and depth on the posterior border of the episcleral plate 2 may be of variable design to accommodate the various extraocular recti muscle insertions (i.e. right medial rectus muscle, left superior rectus muscle, etc.). This embodiment may also be scaled down for pediatric applications.

FIG. 7 is an embodiment of the present invention having a left-sided plate while FIG. 8 is an embodiment of the present invention having a right-sided plate. The FIG. 7 embodiment of the present invention may be accomplished in circumstances where the implant must be positioned such that the episcleral plate 2 lies substantially to the left of the drainage tube 6 adjoined to the episcleral plate 2. Alternately, the FIG. 8 embodiment of the present invention may be accomplished in circumstances where the implant must be positioned such that the episcleral plate 2 lies substantially to the right of the drainage tube 12 adjoined to the episcleral plate 2. In both the left-sided and the right-sided plate configurations, the episcleral plate 2 may be easily folded or rolled upon itself to facilitate implantation into a recipient's eye by rolling the episcleral plate 2 starting at one end of the plate and rolling the episcleral plate 2 towards the other end. This embodiment too may be downsized to accommodate pediatric use.

FIG. 9 is an embodiment of the present invention having a fenestrated plate, i.e. the episcleral plate 2 has apertures located therein. All embodiments of the glaucoma drainage device of the present invention may be modified to further comprise holes located in the episcleral plate 2 as illustratively shown in FIG. 9. The apertures 16 and 18 facilitate maintaining the present invention in its desired location after implantation. The positioning may be accomplished through an intact conjunctiva with a manipulating instrument or may be accomplished through small conjunctival incisions. The episcleral apertures may also be used to secure the episcleral plate 2 in position with sutures or other surgical tissue fasteners. Although the episcleral plate 2 in FIG. 9 has two apertures, namely 16 and 18, other embodiments may have more or less than two apertures. The apertures may vary in number, size and shape—even within a given episcleral plate design to accommodate the potentially variable circumstances encountered during glaucoma drainage device implantation surgery. The apertures in the FIG. 9 extend through the entire thickness of the episcleral plate 2. The apertures may however only extend partially into a surface of the episcleral plate 2 in other contemplated embodiments of the present invention.

The FIG. 11 shows the present invention device in a typical implant application. The device is implanted through an injection-sized scleral incision 26. The episcleral plate 2 is situated atop the sclera 24 beneath the tenon's capsule 28. The drainage tube 12 extends from the episcleral plate through the sclerostomy to provide fluid communication to the anterior chamber of the recipient's eye for drainage of aqueous humor to relieve intraocular pressure in the recipient's eye. The terminal collar further retains and maintains the drainage tube of the device in the proper implanted position.

While the invention has been described and illustrated with reference to specific embodiments thereof, it is understood that other embodiments may be resorted to without departing from the invention. Therefore the form of the invention set out above should be considered illustrative and not as limiting the scope of the following claims.

What I claim is:

1. A glaucoma drainage device implant for drainage of aqueous fluid from a recipient's eye comprising:
   a foldable and rollable episcleral plate that can be sufficiently folded and rolled upon itself for delivery to an implant site through an injection delivery system, thereby minimizing a scleral incision to a needle injection-sized incision;
   a peripheral rim disposed along a peripheral edge of said foldable and rollable episcleral plate; and
   a drainage tube having a first end connected to said episcleral plate and a second free end and a passageway therethrough for fluid communication between the episcleral plate and the recipient's eye;
   whereby said foldable and rollable episcleral plate may be folded and rolled upon itself and delivered to the implant site via an injection delivery system.

2. The glaucoma drainage device of claim 1 wherein said episcleral plate is constructed of bio-compatible materials.

3. The glaucoma drainage device of claim 1 wherein said episcleral plate is constructed of silicon.

4. The glaucoma drainage device of claim 1 wherein said episcleral plate is constructed of a material that has a memory of its unfolded and unrolled shape for resisting permanent deformation of said episcleral plate as said episcleral plate is folded and rolled upon itself for delivery to the implant site via said injection delivery system.

5. The glaucoma drainage device of claim 1 wherein said episcleral plate further comprises resilient veins disposed throughout said episcleral plate for resisting permanent deformation of said episcleral plate while still allowing said episcleral plate to be folded and rolled upon itself for delivery to the implant site via said injection delivery system.

6. The glaucoma drainage device of claim 1 wherein said episcleral plate further comprises inflatable veins disposed throughout said episcleral plate for resisting permanent deformation of said episcleral plate while still allowing said episcleral plate to be folded and rolled upon itself for delivery to the implant site via said injection delivery system.

7. The peripheral rim of claim 1 wherein said peripheral rim is capable of being inflated from a lower profile deflated state to a higher profile inflated state whereby the inflated peripheral rim provides improved volume and filtration characteristics to the glaucoma drainage device.

8. The glaucoma drainage device of claim 7 further comprising an inflation passageway with one end connected to said inflatable peripheral rim for inflation of said inflatable rim.

9. The glaucoma drainage device of claim 8 wherein said inflation passageway is located in intimate contact with said drainage tube.

10. The drainage tube of claim 1 further comprising pressure regulating means for limiting a flow of aqueous fluid through the drainage tube when a pressure exerted thereon is below a predetermined threshold pressure.

11. The glaucoma drainage device of claim 10 wherein said pressure regulating means are pressure sensitive valves that limit the flow of aqueous fluid through the drainage tube when the pressure exerted thereon is below a predetermined threshold pressure.

12. The drainage tube of claim 1 further comprising a water impermeable, pigmented membrane located substantially near the free end of said drainage tube.

13. The glaucoma drainage device implant of claim 1 further comprising a terminal collar located substantially near the free end of said drainage tube for maintaining and retaining said drainage tube at its desired implanted location.

14. The glaucoma drainage device implant of claim 1 further comprising retention bands located along said drainage tube for maintaining and retaining said drainage tube at its desired implanted location and preventing leakage around the drainage tube.

15. The glaucoma drainage device implant of claim 1 further comprising retention rings located along said drainage tube for maintaining and retaining said drainage tube at its desired implanted location and preventing leakage around the drainage tube.

16. The glaucoma drainage device implant of claim 1 wherein said glaucoma drainage device is proportionally sized for implantation in a pediatric eye.

17. The glaucoma drainage device implant of claim 1 further adapted for superior insertion implantation wherein said episcleral plate is shaped along a posterior portion thereof to accommodate various extraocular recti muscles in a recipient's eye without impinging on the various extraocular muscles activity.

18. The glaucoma drainage device implant of claim 1 further adopted for implantation in the recipient's eye wherein said episcleral plate is located either substantially to the right or to the left of said drainage tube.

19. The glaucoma drainage device implant of claim 1 wherein said episcleral plate is fenestrated.

\* \* \* \* \*